United States Patent
Jagadeeswaran (10) Patent No.: US 9,801,886 B2
(45) Date of Patent: Oct. 31, 2017

(54) THROMBOCYTE INHIBITION VIA VIVO-MORPHOLINO KNOCKDOWN OF ALPHA IIB

(75) Inventor: Pudur Jagadeeswaran, Denton, TX (US)

(73) Assignee: University of North Texas, Denton, TX (US)

( * ) Notice: Subject to any disclaimer, the term of this patent is extended or adjusted under 35 U.S.C. 154(b) by 332 days.

(21) Appl. No.: 13/015,905

(22) Filed: Jan. 28, 2011

(65) Prior Publication Data

US 2011/0190287 A1    Aug. 4, 2011

Related U.S. Application Data

(60) Provisional application No. 61/299,052, filed on Jan. 28, 2010.

(51) Int. Cl.
| | |
|---|---|
| *C07D 295/00* | (2006.01) |
| *C40B 30/06* | (2006.01) |
| *C12N 5/00* | (2006.01) |
| *C12N 15/113* | (2010.01) |
| *A61K 31/5377* | (2006.01) |
| *C07D 413/14* | (2006.01) |

(52) U.S. Cl.
CPC ........ *A61K 31/5377* (2013.01); *C07D 413/14* (2013.01); *C12N 5/00* (2013.01); *C40B 30/06* (2013.01)

(58) Field of Classification Search
None
See application file for complete search history.

(56) References Cited

PUBLICATIONS

Kim, et al. (2010) Vivo-Morpholino knockdown of alphaIIb: a novel approach to inhibit thrombocyte function in adult zebrafish. Blood Cells, Molecules, and Diseases, v.44:169-74.*
Hudziak, R.M., et al., "Antiproliferative effects of steric blocking phosphorodiamidate morpholino antisense agents directed against c-myc." Antisense Nucleic Acid Drug Dev. 10 (2000) 163-76.
Cobbs, C.S., et al., "Inactivation of wild-type p53 protein function by reactive oxygen and nitrogen species in malignant glioma cells." Cancer Res. 63 (2003) 8670-3.
Nasevicius, A., et al, Effective targeted gene 'knockdown' in zebrafish. Nat. Genet. 26 (2000) 216-20.
Gregory, M., et al, "Genetic analysis of hemostasis and thrombosis using vascular occlusion." Blood Cells Mol. Dis. 29 (2002) 286-95.
Shestopalov, I.A., et al., "Light-controlled gene silencing in zebrafish embryos." Nat. Chem. Biol. 3 (2007) 650-1.
Morcos, P.A., et al., "Vivo-Morpholinos: a non-peptide transporter delivers Morpholinos into a wide array of mouse tissues." Biotechniques 45 (2008) 613-4, 616, 618 passim.
Moulton, J.D., et al., "Gene knockdowns in adult animals: PPMOs and vivo-morpholinos." Molecules 14 (2009) 1304-23.
Wu, B., et al., "Octa-guanidine morpholino restores dystrophin expression in cardiac and skeletal muscles and ameliorates pathology in dystrophic mdx mice." Mol. Ther. 17 (2009) 864-71.
Shattil, S.J., et al., "Changes in the platelet membrane glycoprotein IIb.IIIa complex during platelet activation." J. Biol. Chem. 260 (1985) 11107-14.
Bennett, J.S., et al., "Interaction of fibrinogen with its platelet receptor. Differential effects of alpha and gamma chain fibrinogen peptides on the glycoprotein IIb-IIIa complex." J. Biol. Chem. 263 (1988) 12948-53.
Jagadeeswaran, P., et al., "Identification and characterization of zebrafish thrombocytes." Br. J. Haematol. 107 (1999) 731-8.
Jagadeeswaran, P., et al., "Zebrafish: a genetic model for hemostasis and thrombosis." J. Thromb. Haemost. 3 (2005) 46-53.
Thattaliyath, B., et al., "Young thrombocytes initiate the formation of arterial thrombi in zebrafish." Blood 106 (2005) 118-24.
Coller, B.S., "Anti-GPIIb/IIIa drugs: current strategies and future directions." Thromb. Haemost. 86 (2001) 427-43.
Keating, F.K., et al., "Augmentation of inhibitory effects of glycoprotein IIb-IIIa antagonists in patients with diabetes." Thromb. Res. 113 (2004) 27-34.
Rothbard, J.B., et al., "Role of membrane potential and hydrogen bonding in the mechanism of translocation of guanidinium-rich peptides into cells." J. Am. Chem. Soc. 126 (2004) 9506-9507.
Futaki, S., et al., "Translocation of branched-chain arginine peptides through cell membranes: flexibility in the spatial disposition of positive charges in membrane-permeable peptides." Biochemistry 41 (2002) 7925-7930.

* cited by examiner

*Primary Examiner* — Jennifer McDonald
(74) *Attorney, Agent, or Firm* — Edwin S. Flores; Daniel J. Chalker; Chalker Flores, LLP (57) ABSTRACT

Novel compounds comprising a guanidine-rich head covalently coupled to one or more oligonucleotide antisense sequences which are useful to modulate blood coagulation by affecting the expression of integrin αIIb or β3 are described herein. This invention also includes pharmaceutical compositions containing these compounds, with or without other therapeutic agents, and to methods of using these compounds as inhibitor of platelet aggregation, as thrombolytics, and/or for the treatment of other thromboembolic disorders. Vivo-MOs, which include eight guanidine groups dendrimerically arranged in the guanidine-rich head and two synthetic antisense morpholino oligonucleotides, are representative compounds of the present invention.

7 Claims, 6 Drawing Sheets

SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide.

<400> SEQUENCE: 1
ggaagtgact aaaccctcac ctcat                                25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide.

<400> SEQUENCE: 2
cctcttacct cagttacaat ttata                                25

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 3
agtgctgcat ggacaaagtg                                      20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 4
ggttctccac ctgttccaga                                      20

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 5

Arg Gly Gly Thr Asp Ile Asp Asp Asn Gly Tyr Pro Asp Leu Ile Ile
1               5                   10                  15

Gly

THROMBOCYTE INHIBITION VIA VIVO-MORPHOLINO KNOCKDOWN OF ALPHA IIB

CROSS-REFERENCE TO RELATED APPLICATIONS

This application claims priority to U.S. Provisional Application Ser. No. 61/299,052, filed Jan. 28, 2010, the entire contents of which are incorporated herein by reference.

STATEMENT OF FEDERALLY FUNDED RESEARCH

This invention was made with U.S. Government support under Contract No. HL077910, awarded by the National Institutes of Health (NIH). The government has certain rights in this invention.

TECHNICAL FIELD OF THE INVENTION

The present invention relates in general to the field of antithrombotic drugs, more particularly, to agents adapted to treat hematological disorders associated with blood cells where the cells have a short half-life. Still more particularly, the invention relates to guanidine-rich dendrimers covalently coupled to morpholino antisense sequences targeting integrin αIIb (Glycoprotein IIb/IIIa) and to methods of using such compounds to affect local expression of integrin αIIb.

REFERENCE TO A SEQUENCE LISTING

The present application includes a Sequence Listing filed separately as required by 37 CFR 1.821-1.825.

BACKGROUND OF THE INVENTION

Without limiting the scope of the invention, its background is described in connection with methods and compositions to modulate blood coagulation.

Antisense oligonucleotides have been used to knockdown protein levels by either translational blocking or splice blocking to control cancer and viral infections with the goal to treat human diseases [1,2]. Knockdown inhibition has been exploited widely in model organisms such as zebrafish, predominantly through use of morpholino oligonucleotides (MOs) to study functions of proteins in both development and disease particularly as a gene discovery tool [3,4]. Typically, these MOs are introduced into the yolks of 1-8-cell-stage zebrafish embryos. Due to the cytoplasmic bridges, it has been thought that MOs rapidly diffuse into these cells allowing ubiquitous cytosolic delivery. However, direct cytosolic delivery of MOs into cells has been difficult to achieve with the exception of microinjections.

Recently, photoactivatable MOs have been introduced to achieve tissue-specific knockdowns in embryos [5]. Another recent development is the conjugation of dendrimeric octaguanidine to MOs (Vivo-MOs) which has resulted in permeability of MOs into cells [6]. Because of this membrane diffusible nature and lack of toxicity, it has been suggested that they might be useful for the use in human therapy [7]. In fact, recently Vivo-MOs have been used to evaluate for use in the treatment of Duchenne Muscular Dystrophy (DMD) [8].

Platelets play a central role in primary hemostasis [9]. During injury, they adhere to subendothelial matrix, become activated, and aggregate to form the primary hemostatic plug. This plug formation involves αIIb or β3 integrin (also known as Glycoprotein IIb/IIIa or Gp IIb/IIIa) activation followed by fibrinogen binding [10,11]. Primary hemostasis in zebrafish also involves thrombocyte aggregation and the fibrinogen receptors as well as thrombocyte functions are all intact in fish [12,13]. These results indicate the technology developed in zebrafish should be translatable to other animal models as well as to humans.

The αIIb or β3 integrin is an adhesion receptor expressed by thrombocytes. This receptor is activated when the thrombocyte is stimulated by ADP, epinephrine, collagen and thrombin. These integrins are essential to the blood coagulation since they have the ability to bind fibrinogen, fibronectin and vitronectin. In patients suffering from Glanzmann's thrombasthenia, an extremely rare coagulopathy, platelets lack glycoprotein IIb/IIIa. Thus, their platelets are less able to adhere to each other and to the underlying tissue of damaged blood vessels. Consequently, no fibrinogen bridging can occur and bleeding time is significantly prolonged.

The αIIb subunit of αIIb integrin is an unparalleled target candidate for inhibition in the primary hemostatic pathway for the following reasons: (i) its inhibition by Vivo-MOs will not cause any non-specific effects of inhibition in other cell types because thrombocytes are the only cells which have αIIb on their membrane surface, (ii) its down regulation could be controlled by the dose of MOs so proper balance of hemostasis could be achieved, (iii) newly generated young thrombocytes will undergo the effect of MOs and the young thrombocytes have previously been shown to initiate thrombus formation at the site of injury, reduction of αIIb in these young thrombocytes could have an immediate effect, (iv) αIIb is the ultimate molecule which receives signals from many pathways and therefore controlled inhibition of this molecule will block the effect of all the pathways, and (vi) it is possible to collect adult thrombocytes, once proof of principle is established for inhibiting thrombocyte function in adult zebrafish, any other candidate factors such as thrombocyte receptors could be targeted for evaluating the function of novel genes involved in hemostatic pathways by studying the biochemical events in thrombocytes.

SUMMARY OF THE INVENTION

The present invention relates to methods and compositions to inhibit thrombocyte function through the targeting of nucleotides capable of modulating the expression of αIIb with guanidine-rich carriers. More specifically, it relates to a time and dose-dependent inhibition of thrombocyte function by αIIb Vivo-MOs. The present invention also shows that a single intravenous injection is sufficient to achieve effective targeting of αIIb in thrombocytes and down-regulation of thrombocyte aggregation concomitant with reduced hemostatic activity.

The invention includes a composition comprising a guanidine-rich head and one or more oligonucleotides encoding one or more sequences capable of hybridizing to a region of the αIIb gene, thereby modulating αIIb gene expression. That region may be coding, non-coding (e.g. an intron) or a region spanning both coding and non-coding sequences of the gene. The oligonucleotides may be natural or synthetic oligonucleotides, such as antisense synthetic morpholino oligonucleotides. One or more of the oligonucleotides may be a morpholino oligonucleotide and one or more of the oligonucleotides may target a splice site of the αIIb gene.

The guanidine-rich head used to deliver the oligonucleotides may contain the guanidine groups dendrimerically arranged. The preferred embodiment of the present invention contains 8 guanidine groups, although other arrangements including between 7 and 15 guanidine groups may also be used. The composition may be designed to modulate the expression of the αIIb gene, or to completely suppress the expression of the gene.

The present invention also relates to combination products, that is, it includes platelet aggregation inhibiting pharmaceutical formulations comprising (i) an effective inhibiting amount of a compound comprising a guanidine-rich head and one or more oligonucleotides encoding one or more sequences capable of hybridizing to a region of the αIIb gene and (ii) a pharmaceutically acceptable carrier or diluent. The oligonucleotides included in the pharmaceutical formulations may be synthetic antisense oligonucleotides. The guanidine-rich head may contain guanidine groups dendrimerically arranged, their number ranging from about 7 to about 15 guanidine groups. Currently preferred examples comprise 8 guanidine groups. One or more of the synthetic antisense oligonucleotides may be a morpholino oligonucleotide and one or more of the synthetic antisense oligonucleotides may target a splice site of the αIIb gene. The pharmaceutical formulations may partially or totally suppress the expression of the αIIb gene.

Another embodiment of the present invention is a method to silence αIIb gene expression in target cells. The method comprises the steps of (i) selecting a cell target and (ii) contacting the cell target with a composition comprising a guanidine-rich head and one or more oligonucleotides encoding one or more sequences capable of hybridizing to a region of the αIIb gene. The oligonucleotides may be synthetic antisense oligonucleotides. In one embodiment, the oligonucleotides may be morpholino oligonucleotides. These oligonucleotides may target a splice site of the αIIb gene.

The guanidine-rich head may contain guanidine groups dendrimerically arranged. The guanidine-rich head may contain 8 guanidine groups, although other arrangements including between about 7 and 15 guanidine groups may also be used. The molecular mechanism mediating the modulation or suppression of the expression of the αIIb may be exon skipping.

The present invention also includes a method of treating a human or another mammal to alleviate or cure the pathological effects of conditions such as atherosclerosis, arteriosclerosis, acute myocardial infarction, chronic stable angina, unstable angina, transient ischemic attacks, strokes, peripheral vascular disease, arterial thrombosis, preeclampsia, embolism, restenosis following angioplasty, carotid endarterectomy, and anastomosis of vascular grafts. The method comprises administering an amount of a composition comprising (i) a guanidine-rich head and (ii) one or more oligonucleotides encoding one or more sequences capable of hybridizing to a region of the αIIb gene, thereby modulating αIIb gene expression. That region may be coding, non-coding (e.g., an intron) or a region spanning both coding and non-coding sequences of the gene. The oligonucleotides may be natural or synthetic oligonucleotides, such as antisense synthetic morpholino oligonucleotides. One or more of the oligonucleotides may be a morpholino oligonucleotide and one or more of the oligonucleotides may target a splice site of the αIIb gene. The guanidine-rich head used to deliver the oligonucleotides may contain the guanidine groups dendrimerically arranged. The preferred embodiment of the present invention contains 8 guanidine groups, although other arrangements including between 7 and 15 guanidine groups may also be used. The composition may be designed to modulate the expression of the αIIb gene or to completely suppress the expression of the gene. The composition can be administered alone or in a combination pharmaceutical formulation, in amounts pharmacologically effective to inhibit the expression of αIIb in the human to a level sufficient to ameliorate the observed pathological effects.

The present invention also includes a method for effecting inhibition of platelet aggregation. The method comprises administering to a mammal in need thereof an effective platelet aggregation inhibiting amount of a composition comprising (i) a guanidine-rich head and (ii) one or more oligonucleotides encoding one or more sequences capable of hybridizing to a region of the αIIb gene, thereby modulating αIIb gene expression. That region may be coding, non-coding (e.g., an intron) or a region spanning both coding and non-coding sequences of the gene. The oligonucleotides may be natural or synthetic oligonucleotides, such as antisense synthetic morpholino oligonucleotides. One or more of the oligonucleotides may be a morpholino oligonucleotide and one or more of the oligonucleotides may target a splice site of the αIIb gene. The guanidine-rich head used to deliver the oligonucleotides may contain the guanidine groups dendrimerically arranged. The preferred embodiment of the present invention contains 8 guanidine groups, although other arrangements including between 7 and 15 guanidine groups may also be used. The composition may be designed to modulate the expression of the αIIb gene or to completely suppress the expression of the gene. The composition can be administered alone or in a combination pharmaceutical formulation, in amounts pharmacologically effective to inhibit the expression of αIIb in the human to a level sufficient to inhibit platelet aggregation.

Another embodiment of the present invention is a method of inhibiting fibrinogen binding. The method comprises contacting cells normally expressing glycoprotein IIb-IIIa with an effective amount of a composition comprising (i) a guanidine-rich head and (ii) one or more oligonucleotides encoding one or more sequences capable of hybridizing to a region of the αIIb gene, thereby modulating αIIb gene expression. That region may be coding, non-coding (e.g., an intron) or a region spanning both coding and non-coding sequences of the gene. The oligonucleotides may be natural or synthetic oligonucleotides, such as antisense synthetic morpholino oligonucleotides. One or more of the oligonucleotides may be a morpholino oligonucleotide and one or more of the oligonucleotides may target a splice site of the αIIb gene. The guanidine-rich head used to deliver the oligonucleotides may contain the guanidine groups dendrimerically arranged. The preferred embodiment of the present invention contains 8 guanidine groups, although other arrangements including between 7 and 15 guanidine groups may also be used. The composition may be designed to modulate the expression of the αIIb gene or to completely suppress the expression of the gene. The composition can be administered alone or in a combination pharmaceutical formulation, in amounts pharmacologically effective to inhibit fibrinogen binding.

In yet another embodiment the present invention describes a method of identifying one or more genes involved in hemostasis, thrombocyte function or both comprising the steps of: (i) generating a library of one or more gene knockdown agents comprising interfering oligonucleotides, (ii) injecting the gene knockdown agents into one or more zebrafish species, (iii) withdrawing a blood sample from the zebrafish species injected with the gene knockdown agents, (iv) determining a qualitative, a quantitative change or both in a clotting of the blood sample from the zebrafish species, wherein the change in the clotting indicates an inhibition of the hemostasis, thrombocyte function or both, (v) isolating one or more thrombocytes from the blood sample, (vi) amplifying one or more αIIb mRNAs from the isolated thrombocytes using Reverse transcription Polymerase Chain Reaction (RT-PCR), and (vii) determining the one or more genes involved in hemostasis, thrombocyte function or both from the amplified αIIb mRNAs. In one aspect of the method the one or more oligonucleotides are synthetic antisense oligonucleotides. In another aspect the one or more of the synthetic antisense oligonucleotides is a morpholino oligonucleotide. In yet another aspect one or more of the synthetic antisense oligonucleotides target a splice site of an αIIb gene.

BRIEF DESCRIPTION OF THE DRAWINGS

For a more complete understanding of the features and advantages of the present invention, reference is now made to the detailed description of the invention along with the accompanying figures and in which:

FIGS. 3A and 3B shows the time and dose-dependent inhibition of thrombocyte function by αIIb Vivo-MOs.

FIGS. 4A and 4B show the time and dose-dependent inhibition of normal splicing of αIIb transcripts by αIIb Vivo-MOs.

FIGS. 5A and 5B show immunofluorescence assays of thrombocytes: FIG. 5A shows representative images of immunofluorescence of thrombocytes probed with rabbit antisera zebrafish αIIb peptide polyclonal antibodies. FIG. 5A, panel A, shows images of thrombocytes treated with control Vivo-MOs. FIG. 5A, panel B, shows images of thrombocytes treated with αIIb Vivo-MOs. The left and right columns in Panels A and B are bright field and fluorescence images respectively. Arrows show thrombocytes which are translucent with mostly nucleus and very little cytoplasm; the other cells are erythrocytes.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The term "oligonucleotide" refers to a polymeric molecule having a backbone which supports bases capable of hydrogen bonding to typical nucleic acids, where the polymer backbone presents the bases in a manner to permit such hydrogen bonding in a sequence specific fashion between the oligonucleotide and a typical nucleic acid (e.g., single-stranded RNA, double-stranded RNA, single stranded DNA or double stranded DNA). "Oligonucleotides" include polymers with nucleotides which are an N- or C-glycoside of a purine or pyrimidine base, and polymers containing non-standard nucleotide backbones, for example, backbones formed using phosphorodiamidate morpholino chemistry, polyamide links (e.g., peptide nucleic acids or PNAs) and other synthetic sequence-specific nucleic acid molecules.

An "antisense oligonucleotide" refers to a molecule which includes a sequence of purine and pyrimidine heterocyclic bases supported by a backbone that allows the antisense oligomer to hybridize to a target nucleic acid (e.g., RNA) sequence by Watson-Crick base pairing, to form a nucleic acid:oligomer heteroduplex within the target sequence. Typically, such an oligomer is from 8 to about 50 nucleotide subunits long, and more typically about 12 to 30 nucleotide subunits long. The oligomer may have the exact sequence complementarity to the target sequence or near complementarity. Such an antisense oligomer may completely or partially block or inhibit the formation of a specific protein by binding to a double-stranded or single-stranded portion of the gene encoding said specific protein. The binding between the antisense oligonucleotide and target gene can inhibit or modulate mRNA translation, gene splicing, and/or protein synthesis.

A "morpholino oligonucleotide" (MO) refers to an oligonucleotide analog a backbone which supports bases capable of hydrogen bonding to typical polynucleotides, wherein the oligomer contains, instead of a pentose sugar backbone moiety as found in nucleic acids a morpholino backbone moiety, with coupling through the ring nitrogen. A typical morpholino oligonucleotide is composed of morpholino subunits where the subunits are linked together by phosphorus-containing linkages, one to three atoms long, joining the morpholino nitrogen of one subunit to the 5' exocyclic carbon of an adjacent subunit, and each subunit contains a purine or pyrimidine base-pairing moiety effective to bind, by base-specific hydrogen bonding, to a base in a polynucleotide.

The term "dendrimer" refers to an organic compound that has at least one branched tree-like structure originating from at least one core atom or at least one core portion of a molecule. The branches of a dendrimer may be structurally similar or dissimilar to one another.

The term "modulating," relative to the effect of compositions containing antisense oligonucleotides on gene expression, refers to the enhancement or reduction of the expression of a given protein as result of interference with the transcription or translation of the nucleic acid sequence, which encodes that protein.

An "effective amount" refers to the amount of guanidine-rich head:synthetic oligonucleotide composition (e.g., a Vivo-MO) administered to a mammalian subject, either as a single dose or as part of a series of doses, that is effective to inhibit a biological activity, e.g., the expression of a selected target nucleic acid sequence.

To "treat" an individual or a cell is any type of intervention provided as a way to alter the natural course of the individual or cell. Treatment includes, but it is not limited to, administration of e.g., a pharmaceutical composition, and may be performed prophylactically, or subsequent to the initiation of a pathological event.

Knockdown of protein function by antisense oligonucleotides has been used to understand the protein function not only in development but also in human diseases. Recently, Vivo-Morpholinos, chemically modified morpholinos which penetrate the cells, have been used in adult animal models to alter the splicing and thereby change the protein expression. Until now, there have been no such studies using Vivo-Morpholinos, to evaluate hemostatic function in adult animals.

The present invention shows that it is possible to inhibit thrombocyte specific function by exon skipping. This principle was demonstrated using αIb Vivo-MOs in adult zebrafish. αIIb Vivo-Morpholinos were injected intravenously into adult zebrafish. Thrombocyte function was assayed by time to aggregation assay of the citrated blood, annexin V binding to thrombocytes, and gill bleeding. The thrombocyte functional inhibition occurred in 24 hrs after αIIb Vivo-Morpholinos injection and reached a maximum in 48 hrs. However, in 72 hrs, the inhibition was no longer observed. Reduction of annexin V binding to thrombocytes and increased gill bleeding were observed 48 hrs after IA % Vivo-Morpholino injections. The action of the αIIb Vivo-Morpholino was demonstrated by the presence of an alternatively spliced αIIb mRNA and the reduction of αIIb in thrombocytes of fish treated with αIIb Vivo-Morpholino.

The findings of the present invention provide the first proof of principle that thrombocyte function can be inhibited by thrombocyte-specific Vivo-Morpholinos in adult zebrafish. The present invention presents an approach to knockdown thrombocyte-specific genes to conduct biochemical studies in thrombocytes. This study also provides the first antisense antithrombotic approach to inhibit thrombocyte function in adult zebrafish.

Zebrafish antisense injections to generate knockdowns: An antisense αIIb Vivo-MO was designed. This antisense, containing the nucleic acid sequence 5'-GGAAGTGACTAAACCCTCACCTCAT-3' (SEQ ID NO: 1), targets the donor splice site of exon 20 of the zebrafish αIIb gene. The antisense sequence was submitted to Gene-Tools LLC, Philomath, Oreg. for synthesis. A control Vivo-MO 5'-CCTCTTACCTCAGTTACAATTTATA-3' (SEQ ID NO: 2) was also purchased from Gene-Tools. Zebrafish were anesthetized and approximately 5 µl Vivo-MOs (either the original solution supplied by the vendor, 0.5 mM or 0.05 mM diluted with phosphate buffered saline, pH 7.4 (PBS) were taken into a 27 Gauge×1¼ inch needle (27 G1¼ needle) such that the only Vivo-MO solution remained in the needle. For injection, the needle was placed into the region that is located between the second and third body stripes closer to the anal pore and at right angles to the location of the inferior vena cava. It was then gently pushed to insert it into the blood vessel, the syringe piston was immediately pushed gently to inject the contents.

Blood sample preparation and thrombocyte functional assays: Blood collection was performed by gently poking the lateral surface of the fish body where the caudal artery and the caudal vein anastamose with the 27 $G1_{1/4}$ needle. A micropipette set was used for collecting 1 µL blood welling out from the vessel. This 1 µl blood was immediately dispensed into a 0.5 ml Eppendorf tube containing 1 µl 3.8% sodium citrate in PBS. For qualitative study, the thrombocyte aggregation assay was performed by adding 1 µl of citrate-buffered blood to 8 µl 0.63% sodium citrate in PBS and 1 µl ADP reagent (200 µM, Sigma-Aldrich, St. Louis, Mo.) in a conical well of the microtiter plate [12]. The plate was tilted manually every 5 min for 1 to 1.5 hrs at 25° C. to determine the time taken to stop the flow of blood down the walls of the well, i.e., time taken for aggregation of thrombocytes (TTA). For quantitative study, the thrombocyte aggregation assay was performed without ADP reagent.

For detecting annexin V binding, cells from heparinized blood (2 µl blood collected into 2 µl 20 mg heparin in 1 ml PBS pH 7.4) were used. To this blood, 1 µl of ADP reagent or 1 µl of PBS as the control was added, and the cells were incubated for 3 min at 25° C. The cells were fixed immediately with 10 µl 4% paraformaldehyde and to this mixture 2 µl of 10× annexin binding buffer and 3.5 µl of annexin V-FITC (BD Biosciences, San Jose, Calif.) were added and incubated in the dark at 25° C. for 1 minute. After annexin V probing, the cells were smeared on a slide and kept under a cover slip, and the fluorescent images of thirty thrombocytes were taken using a Nikon Eclipse 80i microscope with excitation at 450-490 nm with constant exposure times. The average intensity of thrombocytes was plotted as levels of annexin V binding [14].

Gill bleeding was induced by placing the fish in 50 µM NaOH. The fish were anesthetized with 2 mM tricaine (Sigma-Aldrich, St. Louis, Mo.) for 3 minutes prior to placing them in NaOH. The fish were photographed with a Nikon E995 Coolpix camera and the red pixels were counted by Adobe Photoshop software 7.0 as a measure of bleeding.

Reverse transcription Polymerase Chain Reaction (RT-PCR): Zebrafish thrombocytes in whole blood were labeled with mepacrine as previously described [14]. The blood was diluted and placed on the microscopic slide so that thrombocytes were well separated from other cells. Five hundred thrombocytes were pipetted using a Nanoject II micropipette (Drummond Scientific Company, Broomal, Pa.) under Nikon Eclipse 80 microscope (with excitation at 450-490 nm) and were used in cell to cDNA kit (Agilent Technologies, La Jolla, Calif.) to amplify the αIIb mRNA. Forward, 5'-AGTGCTGCATGGACAAAGTG-3' (SEQ ID NO: 3), and reverse, 5'-GGTTCTCCACCTGTTCCAGA-3' (SEQ ID NO: 4), primers for exons 18 and 22, respectively, were designed. These primers were synthesized by Biosynthesis, Lewisville, Tex. They were used to amplify the 396 bp product. In the case of exon skipping, the predicted product is a 149 base pair. These RT-PCR products were resolved on 1.5% agarose gels and their DNA sequences were determined by Lone Star Labs, Houston, Tex. The density of RT-PCR products was measured using the Quantity One software from Bio-Rad Laboratories, Inc. Hercules, Calif. Since the 149 bp band is 2.5 times smaller than the 396 bp band, the intensity of the 149 bp band was multiplied by 2.5 so the bands have molar equivalent intensities. Relative percentages were calculated by using the sum of the intensity of the 396 bp and the corrected intensity of the 149 bp band as 100%.

Immunostaining of Thrombocytes: Immunofluorescence was performed on freshly prepared blood smears from control and αIIb Vivo-MO injected zebrafish. The slides were fixed with 70% cold ethanol for 15 minutes, and rinsed with PBS three times. 20 µl of 1 mg/ml rabbit polyclonal antisera against the zebrafish αIIb peptide RGGTDID-DNGYPDLIIG (Custom made by Alpha Diagnostic, Inc., San Antonio, Tex.) (SEQ ID NO: 5) were incubated with blood cells under a cover slip for 1.5 hrs at 25° C. To minimize evaporation the slides were kept in a sealed plastic bag. After removal of the cover slip, the slides were rinsed with PBS three times and then incubated with FITC-conjugated rabbit anti-sheep IgG (Sigma-Aldrich, St. Louis, Mo.) for 1.5 hr. The slides were rinsed again with PBS followed by a brief rinse with water, then photographed for immunofluorescence using a Nikon Eclipse 80i microscope. The intensities of the immunofluorescent thrombocytes were quantitated by NIS-Elements AR 2.30 software from Nikon.

Statistical Analysis: Statistical analysis was performed using Sigma Plot 10 with Sigma Stat integration software. Statistical significance was assessed by ANOVA and a P value<0.05 was considered significant.

Figure 1:
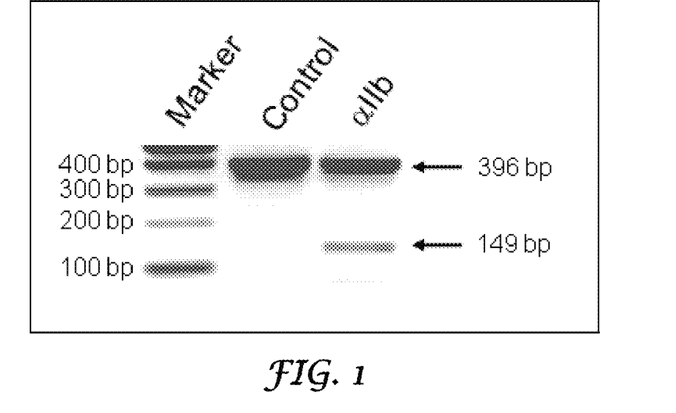
FIG. 1 shows αIIb Vivo-MO induced alternative splicing resulting in deletion of exon 20 encoding fibrinogen binding site. The agarose gel shows the RT-PCR products from thrombocytes isolated from adult zebrafish injected with control Vivo-MO (Control) and αIIb Vivo-MO (αIIb). Arrows show bands corresponding to the normal splice product (396 bp) and alternatively spliced product (149 bp). The 2-log DNA Ladder (New England Biolabs, Ipswich, Mass.) used as DNA size markers (Marker) is in the left lane.

To inhibit the synthesis of αIIb by knockdown method, splicing out exon 20 of αIIb pre-mRNA was chosen because the fibrinogen binding site that is critical for the function of αIIb is within this exon. Direct injection of αIIb Vivo-MOs into the bloodstream allows MOs to penetrate thrombocytes, and the exclusion of exon 20 in the newly synthesized αIIb results in a reduction in the number of functional αIIb molecules, thereby reducing the thrombocyte aggregation potential. This was proven by injecting 5 µl of 0.5 mM αIIb Vivo-MO intravenously into adult zebrafish and after 24 hrs thrombocytes were isolated by pipetting them individually under the microscope using the Nanoject II. These thrombocytes were analyzed for the alternative splicing by using primers designed from exon 18 and 22 on RNA prepared from these thrombocytes. If the normal splicing had occurred this should yield a 396 bp product. If the exon skipping had occurred, this should have yielded a 149 bp of DNA. As expected, a 149 bp band in the thrombocytes of zebrafish was obtained where αIIb Vivo-MOs were injected compared to control Vivo-MOs. This result was also confirmed by sequencing the DNA from these bands (FIG. 1).

Figure 2:
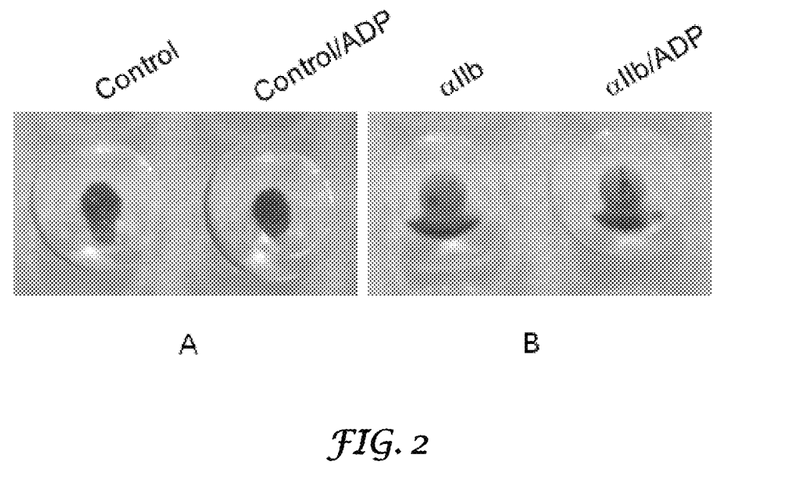
FIG. 2 shows a thrombocyte aggregation assay using adult fish citrate-buffered blood collected after treatment with αIIb Vivo-MOs. Panels A and B show the comparison of blood samples obtained from fish injected with control Vivo-MOs and αIIb Vivo-MOs without ADP agonist (Control and αIIb) and with ADP agonist (Control/ADP and αIIb/ADP), respectively.

To test the aggregation potential of the thrombocytes treated with αIIb Vivo-MO, blood was collected twenty four hours after treatment with αIIb Vivo-MOs. This blood was then used in a whole blood thrombocyte aggregation assay in presence of ADP. The blood collected from control Vivo-MO injected fish did not aggregate when the plate was tilted after 40 min, while it aggregated completely in the presence of ADP (Panel A). However, the αIIb Vivo-MO treated fish blood did not aggregate in either the absence or in the presence of ADP, indicating that the αIIb Vivo-MO is inhibiting thrombocyte aggregation (Panel B).

Figure 3A:
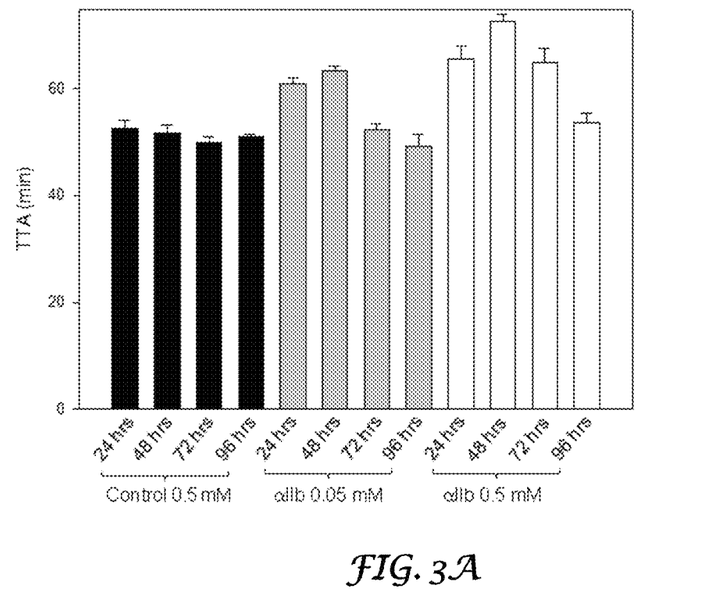
FIG. 3A shows time after injection of Vivo-MOs and time taken to complete aggregation (TTA) on X and Y-axes, respectively. Control represents the control Vivo-MO injections and αIIb represents αIIb Vivo-MO injections. P-values show the significance between respective controls and samples collected after 24 hrs, 48 hrs, 72 hrs and 96 hrs and they are 0.009, 0.003, 0.234, and 0.502 (for 0.05 mM Vivo-MO treatment) and 0.009, <0.001, 0.006 and 0.242 (for 0.5 mM Vivo-MO treatment), respectively.

To further quantitate the aggregation potential of the thrombocytes treated with αIIb Vivo-MO, blood was collected every twenty four hours after treatment with αIIb Vivo-MOs, which was then used in whole blood thrombocyte aggregation assay in absence of ADP reagent. The blood from the treated fish took longer time to aggregate compared to control fish in samples obtained after 24 and 48 hours. In 48 hrs αIIb Vivo-MO was the most effective. However, at 72 hrs after injection the effect of αIIb Vivo-MOs was reduced and at 96 hrs it was not pronounced reaching almost control Vivo-MO values. Also, different doses of αIIb Vivo-MOs were used to show that the aggregation was proportionately decreased to the dose (FIG. 3A). At 0.5 mM dose 72 hrs-sample, although demonstrated decreased aggregation compared to 48 hrs-sample there was still respectable inhibition of aggregation compared to the corresponding 72 hrs-sample that received 0.05 mM dose.

Figure 3B:
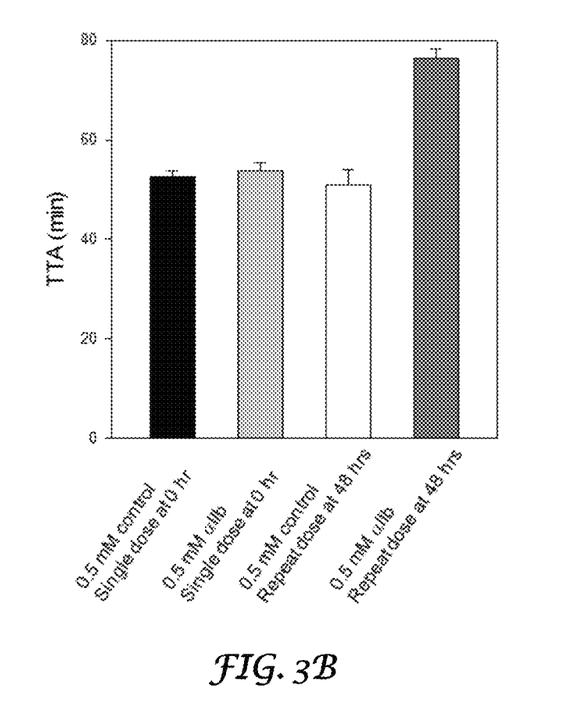
FIG. 3B shows TTA at 96 hrs after Vivo-MO injections. Control represents the control Vivo-MO injections and αIIb represents αIIb Vivo-MO injections. N=6 for all the samples.

A second dose of αIIb Vivo-MOs at 48 hrs was tested to ascertain whether it would maintain the effect of MOs. 0.5 mM αIIb Vivo-MOs was injected 48 hrs after the first injection and found that the inhibition of thrombocyte aggregation was maintained at 96 hrs. The inhibition was similar to that found at 48 hrs. In contrast, when a second dose was not administered, there was a decline in inhibition as shown in FIG. 3A and FIG. 3B.

Figure 4A:
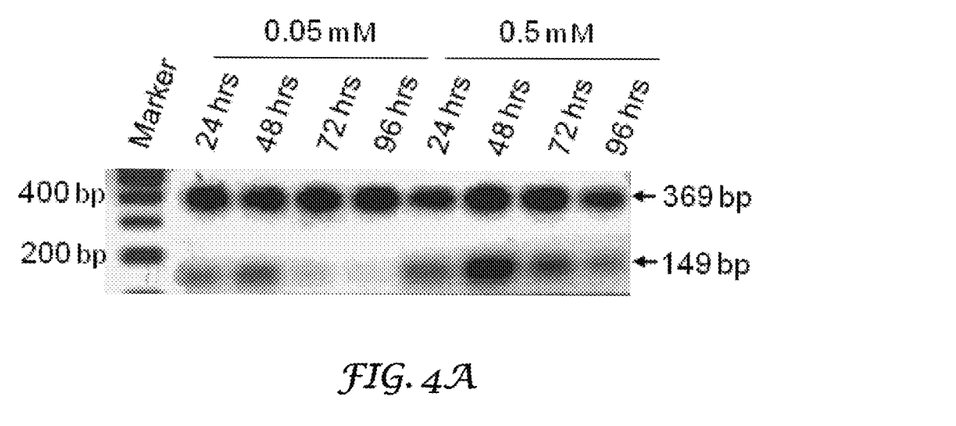
FIG. 4A presents an agarose gel showing the time and dose-dependent inhibition of normal splicing represented by the presence of 149 bp band corresponding to alternatively spliced product. Electrophoretic samples from the two different concentrations (0.05 mM and 0.5 mM) of αIIb Vivo-MOs were used in intravenous injections. Arrows show bands corresponding to the normal splice product (396 bp) and alternatively spliced product (149 bp). The 2-log DNA Ladder (New England Biolabs, Ipswich, Mass.) used as DNA size markers (Marker) is in left lane, FIG. 4B showing the quantitation of 396 bp and 149 bp bands. The numbers in bold are the actual intensities and the numbers in parentheses are the relative percentages.
Figure 4B:
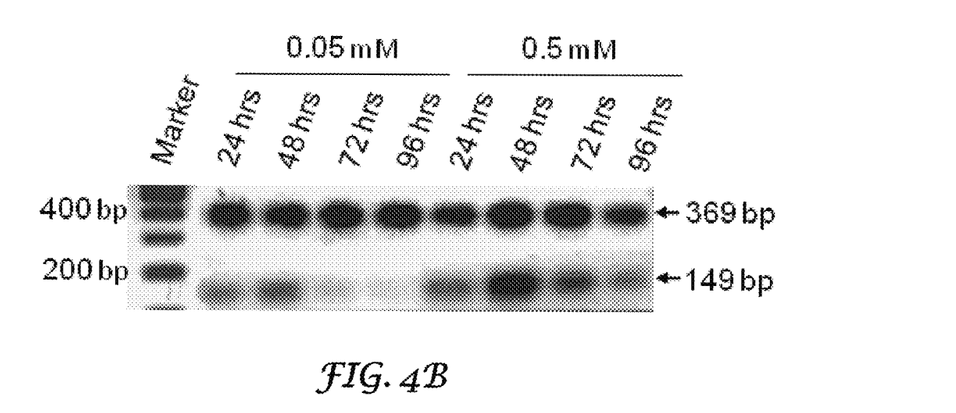

The RT-PCR analysis of blood cells also showed an increase in the 149 bp alternative splice product corresponding to the loss of thrombocyte function (FIG. 4A). The intensities of the bands corresponding to unspliced and alternatively spliced mRNA were measured by image analysis. The results showed that the alternatively spliced mRNA is about 50% in the second day as shown in FIG. 4B. The relative percentages of the 396 bp band and the 149 bp band are shown in FIG. 4B.

Figure 5A:
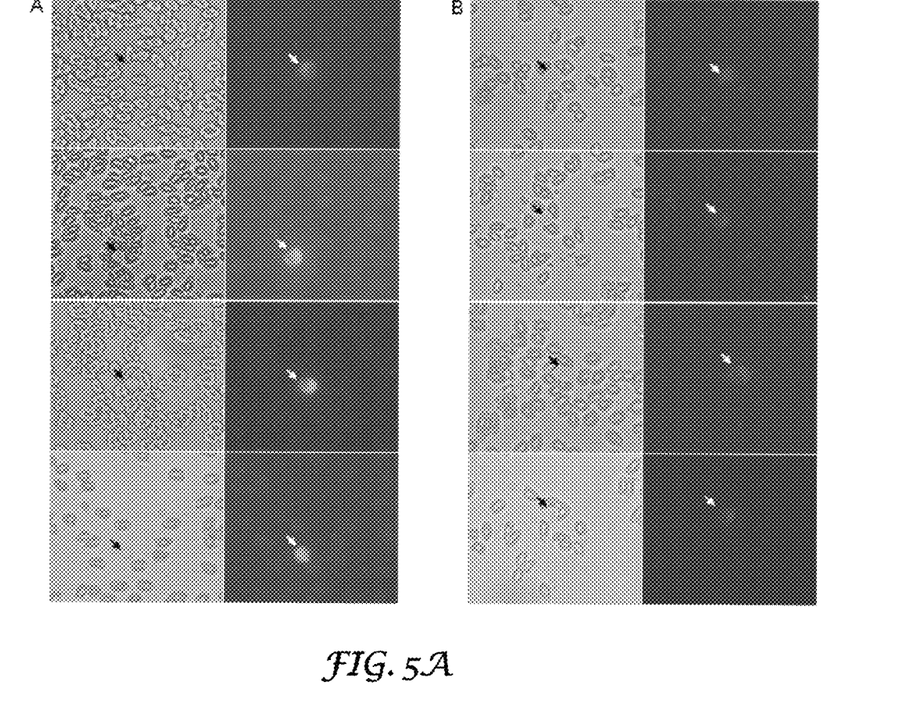
Figure 5B:
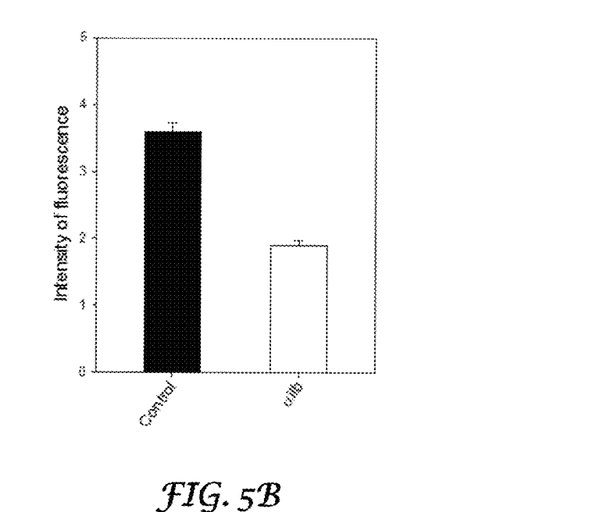
FIG. 5B shows intensity of fluorescence of thrombocytes (N=100) in control Vivo-MO treated (control) and αIIb Vivo-MO (αIIb) measured using image analysis programs.

To test whether the above reduction in mRNA producing αIIb also resulted in reduction in αIIb in thrombocytes, the fishes were treated with 0.5 mM αIIb Vivo-MOs for 48 hrs. Subsequently, the thrombocytes were probed with a primary antibody raised against zebrafish αIIb peptide followed by secondary antibody labeled with FITC (FIG. 5A). These thrombocytes were then compared to the thrombocytes derived from fish injected with control Vivo-MOs, which were probed similarly. The fluorescence intensities of thrombocytes representing the amount of αIIb were measured. The results demonstrated the intensity of thrombocytes treated with αIIb Vivo-MOs was about 65% of the intensity of control Vivo-MO treated fish (FIG. 5B).

Figure 6:
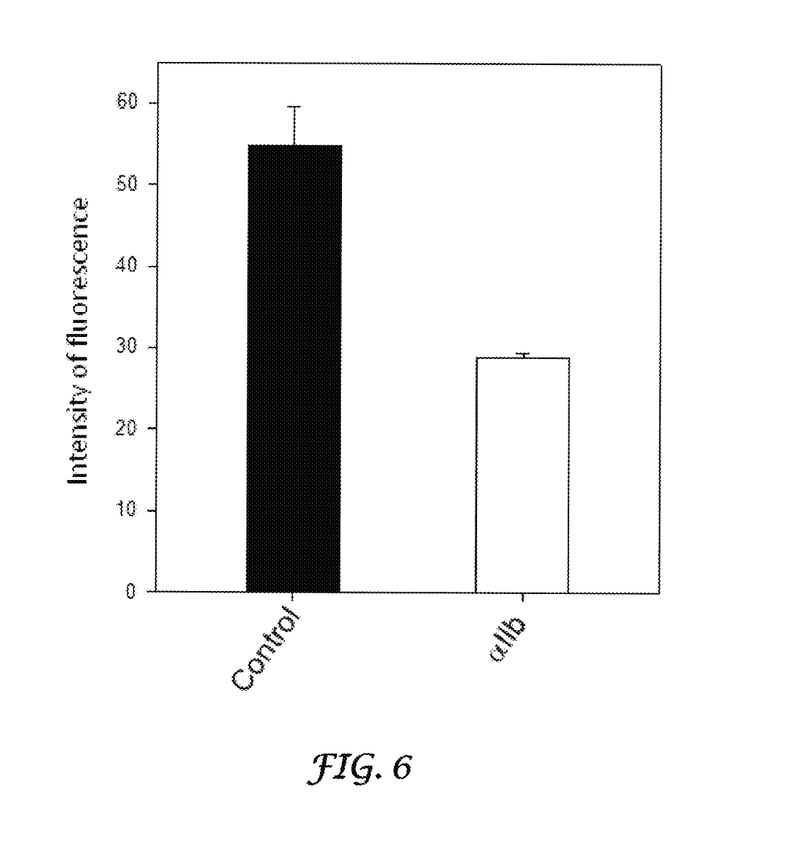
FIG. 6 shows the results of an annexin binding assay. The intensity of fluorescence of thrombocytes (N=30) in control Vivo-MO treated (control) and αIIb Vivo-MO (αIIb) was measured using image analysis programs. P value is <0.001 between the control and αIIb.
Figure 7:
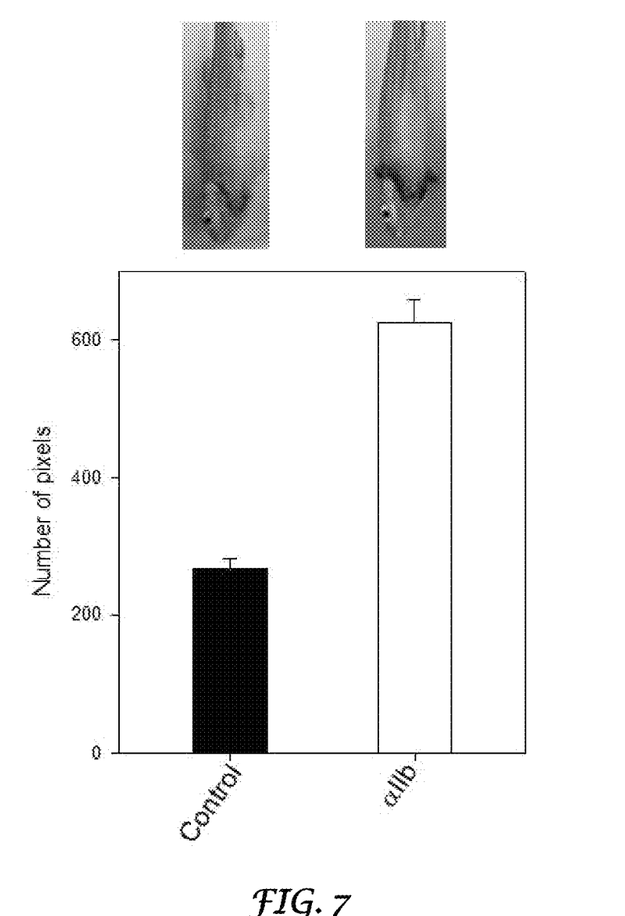
FIG. 7 shows the results of a gill bleeding assay. Fish were photographed and the number of red pixels representing the bleeding were measured in control Vivo-MO treated (control) and αIIb Vivo-MO treated (αIIb) zebrafish (N=6). P value is <0.001 between the control and αIIb.

To provide further evidence on the inhibition of function of these thrombocytes treated with αIIb Vivo-MOs, thrombocyte function was tested by using an annexin V binding assay. Thrombocytes treated with αIIb Vivo-MOs for 48 hrs showed less annexin V binding compared to thrombocytes treated with control Vivo-MO (FIG. 6). Similarly, in the gill bleeding assay, the fish treated with αIIb Vivo-MOs exhibited more bleeding compared to the fish treated with control MOs (FIG. 7).

These results demonstrate that direct injection of αIIb Vivo-MOs intravenously into zebrafish inhibit αIIb and thus reduce thrombocyte aggregation. The RT-PCR results show that alternatively spliced αIIb mRNA is generated, resulting in a 149 bp product. This observation was confirmed by sequence analysis and provides evidence that Vivo-MO is effectively penetrating thrombocytes. The effect of αIIb Vivo-MO on thrombocyte aggregation was observed in 24 hrs, which indicates that the αIIb produced from the alternatively spliced product is replaced within this short period of time. One interpretation is that since thrombocytes have a shorter half life of 4.5 days (unpublished data), they are being rapidly replaced. Another hypothesis is that young thrombocytes which are newly synthesized contain reduced levels of functional αIIb. Since young thrombocytes initiate aggregation and may have functionally reduced αIIb levels, the overall aggregation is reduced. However, since αIIb Vivo-MO treated thrombocytes had overall reduction of annexin V binding to thrombocytes, the former explanation is more likely. The observed overall reduction of antibody binding, to all thrombocytes, in contrast to a reduction in a few thrombocytes supports this hypothesis.

Thrombocytes are produced in kidney marrow in fishes in contrast to bone marrow in mammals. Indeed, it has been shown that the transcription factor controlling megakaryocyte production is present in thrombocytes and blocking this factor reduced the synthesis of thrombocytes. Thus, the principle of reducing the thrombocytes' function by direct injection of Vivo-MOs into the blood should be translatable for mammalian megakaryocytes and thereby the platelet function could be modulated.

The results of the present invention also show that the thrombocyte-aggregation effect of αIIb Vivo-MOs was reduced significantly by the third day after injection. It is possible that Vivo-MOs are being cleared rapidly by either kidneys or by detoxification mechanisms and therefore the thrombocyte-aggregation effect of αIIb Vivo-MOs was not observed. In fact, the increased inhibition of aggregation in 72 hrs-sample that received higher dose of αIIb Vivo-MO compared to the 72 hrs-sample that received the low dose argues in favor of clearance because the higher dose probably takes longer time to clear.

Various αIIb antagonists such as abciximab (ReoPro), tirofiban (Aggrastat), and eptifibatide (Integriling) have been used as inhibitors of αIIb function [15]. Also in diabetic individuals who have thrombotic tendencies, these inhibitors have been suggested [16]. These antagonists are frequently used during percutaneous coronary interventions (angioplasty with or without intracoronary stent placement). They may also be used to treat acute coronary syndromes, without percutaneous coronary intervention, depending on TIMI risk (TIMI, Thrombolysis In Myocardial Infarction; 'TIMI risk' estimates mortality following acute coronary syndromes).

Vivo-MOs are non-toxic and inhibit αIIb synthesis. This evidence indicates that morpholino based approaches can be effectively used to treat thrombosis. This approach is particularly suitable because the thrombocyte or megakaryocyte/platelet is the only cell type making detectable levels of αIIb. This approach of inhibition of αIIb disclose in the present invention may be used in mammalian models because αIIb Vivo-MO may target megakaryocytes before the production of platelets.

The inhibition of αIIb in adult zebrafish provides therapeutic possibilities as well as providing the ability to inhibit the function of any thrombocyte specific gene and perform biochemical studies because thrombocytes are readily accessible. For example, thrombocyte surface receptors such as ADP receptors, thromboxane receptors, other GPCRs and several signaling molecules such as kinases could be inhibited. Thus, this method has the advantage of inhibiting molecules for which small molecule inhibitors are not currently available in resolving biochemical pathways. Furthermore, because of the ease in injections and thrombocyte assays, large scale high throughput knockdowns can be designed to identify novel genes participating in thrombocyte development and function. In addition, the same principles could be used to understand other hematological disorders as well as disorders that are amenable for studies by simple injections of MOs.

This proof of principle of inhibition of αIIb in adult zebrafish by Vivo-MOs has remarkable applicability not only to identify functions of novel genes in thrombocytes but also in other accessible blood cells. Since it is possible to deliver Vivo-MOs to any hematopoietic cells it should be possible to use these reagents not only as an antithrombotic agents but also in correcting other hematological disorders.

In this respect, Vivo-MOs could be used in humans to alleviate the pathological effects of conditions such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angioplasty, carotid endarterectomy, and anastomosis of vascular grafts. αIIb is also known to be overexpressed in metastatic tumor cells. Thus, the compounds or combination products of the present invention may also be useful for the treatment, including prevention, of metastatic cancer.

The application of the principles shown in the present invention can be extended beyond the use of Vivo-MOs. Vivo-MOs contain eight guanidine head groups on two of the side chains of a triazine core, leaving the third side chain of the triazine for conjugation to the morpholino oligomer. Seven to 15 guanidine head groups are optimal for efficient uptake into cells [17], with 8 guanidine head groups exhibiting the most efficient internalization [18]. One artisan would appreciate that morpholinos with different numbers of guanidine head groups would be adequate to achieve similar results. Furthermore, the antisense portion of the Vivo-MO may be replaced with other types of antisense oligonucleotides.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. R. M. Hudziak, J. Summerton, D. D. Weller, and P. L. Iversen, Antiproliferative effects of steric blocking phosphorodiamidate morpholino antisense agents directed against c-myc. Antisense Nucleic Acid Drug Dev. 10 (2000) 163-76.
2. C. S. Cobbs, T. R. Whisenhunt, D. R. Wesemann, L. E. Harkins, E. G. Van Meir, and M. Samanta, Inactivation of wild-type p53 protein function by reactive oxygen and nitrogen species in malignant glioma cells. Cancer Res. 63 (2003) 8670-3.
3. A. Nasevicius, and S. C. Ekker, Effective targeted gene 'knockdown' in zebrafish. Nat. Genet. 26 (2000) 216-20.
4. M. Gregory, R. Hanumanthaiah, and P. Jagadeeswaran, Genetic analysis of hemostasis and thrombosis using vascular occlusion. Blood Cells Mol. Dis. 29 (2002) 286-95.
5. I. A. Shestopalov, S. Sinha, and J. K. Chen, Light-controlled gene silencing in zebrafish embryos. Nat. Chem. Biol. 3 (2007) 650-1.
6. P. A. Morcos, Y. Li, and S. Jiang, Vivo-Morpholinos: a non-peptide transporter delivers Morpholinos into a wide array of mouse tissues. Biotechniques 45 (2008) 613-4, 616, 618 passim.
7. J. D. Moulton, and S. Jiang, Gene knockdowns in adult animals: PPMOs and vivo-morpholinos. Molecules 14 (2009) 1304-23.
8. B. Wu, Y. Li, P. A. Morcos, T. J. Doran, P. Lu, and Q. L. Lu, Octa-guanidine morpholino restores dystrophin expression in cardiac and skeletal muscles and ameliorates pathology in dystrophic mdx mice. Mol. Ther. 17 (2009) 864-71.
9. A. D. Michelson, Platelets, Academic Press/Elsevier, Amsterdam; Boston, 2007.
10. S. J. Shattil, J. A. Hoxie, M. Cunningham, and L. F. Brass, Changes in the platelet membrane glycoprotein IIb.IIIa complex during platelet activation. J. Biol. Chem. 260 (1985) 11107-14.
11. J. S. Bennett, S. J. Shattil, J. W. Power, and T. K. Gartner, Interaction of fibrinogen with its platelet receptor. Differential effects of alpha and gamma chain fibrinogen peptides on the glycoprotein IIb-IIIa complex. J. Biol. Chem. 263 (1988) 12948-53.
12. P. Jagadeeswaran, J. P. Sheehan, F. E. Craig, and D. Troyer, Identification and characterization of zebrafish thrombocytes. Br. J. Haematol. 107 (1999) 731-8.
13. P. Jagadeeswaran, M. Gregory, K. Day, M. Cykowski, and B. Thattaliyath, Zebrafish: a genetic model for hemostasis and thrombosis. J. Thromb. Haemost. 3 (2005) 46-53.
14. B. Thattaliyath, M. Cykowski, and P. Jagadeeswaran, Young thrombocytes initiate the formation of arterial thrombi in zebrafish. Blood 106 (2005) 118-24.
15. B. S. Coller, Anti-GPIIb/IIIa drugs: current strategies and future directions. Thromb. Haemost. 86 (2001) 427-43.
16. F. K. Keating, D. A. Whitaker, B. E. Sobel, and D. J. Schneider, Augmentation of inhibitory effects of glycoprotein IIb-IIIa antagonists in patients with diabetes. Thromb. Res. 113 (2004) 27-34.
17. J. B. Rothbard, T. C. Jessop, R. S. Lewis, B. A. Murray, and P. A. Wender. Role of membrane potential and hydrogen bonding in the mechanism of translocation of guanidinium-rich peptides into cells. J. Am. Chem. Soc. 126 (2004) 9506-9507.
18. S. Futaki, I. Nakase, T. Suzuki, Z. Youjun, and Y. Sugiura. Translocation of branched-chain arginine peptides through cell membranes: flexibility in the spatial disposition of positive charges in membrane-permeable peptides. Biochemistry 41 (2002) 7925-7930.

What is claimed is:

1. A method of identifying a gene involved in hemostasis comprising the steps of:
creating a library of knockdown agents, wherein each knockdown agent comprises an individual interfering antisense morpholino oligonucleotide that targets a specific zebrafish gene;
injecting intravenously an individual knockdown agent from the library of knockdown agents into an individual zebrafish, thereby knocking down expression of a specific zebrafish gene in the individual zebrafish;
withdrawing a blood sample from the individual zebrafish;
determining a quantitative and/or qualitative change in clotting in the blood sample relative to that of a control sample, thereby identifying the specific zebrafish gene as a gene involved in hemostasis; and
identifying a human homolog of the specific zebrafish gene.

2. The method of claim 1, wherein the individual knockdown agent targets a splice site of αIIb.

3. The method of claim 1, wherein each individual interfering antisense morpholino oligonucleotide of the library of knockdown agents comprises a guanidine-rich head.

4. The method of claim 3, wherein the guanidine-rich head contains dendrimerically arranged guanidine groups.

5. The method of claim 3, wherein the guanidine-rich head contains between 7 and 15 guanidine groups.

6. The method of claim 3, wherein the guanidine-rich head contains 8 guanidine groups.

7. A method of identifying a gene involved in thrombocyte function comprising the steps of:
creating a library of knockdown agents, wherein each knockdown agent comprises an individual interfering antisense morpholino oligonucleotide having a guanidine-rich head of between 7 and 15 guanidine groups, wherein each individual interfering antisense morpholino oligonucleotide targets a specific zebrafish gene involved in thrombocyte function;
injecting intravenously an individual knockdown agent from the library of knockdown agents into an individual zebrafish, thereby knocking down expression of a specific zebrafish gene in the individual zebrafish;
withdrawing a blood sample from the individual zebrafish injected with the individual knockdown agent;
determining a quantitative and/or qualitative change in thrombocyte function in the blood sample relative to that of a control sample, thereby identifying the specific zebrafish gene as a gene involved in hemostasis; and
identifying a human homolog of the specific zebrafish gene.

* * * * *